(12) United States Patent
Renaud et al.

(10) Patent No.: US 8,513,410 B2
(45) Date of Patent: Aug. 20, 2013

(54) PROCESS FOR THE SYNTHESIS OF IVABRADINE AND ADDITION SALTS THEREOF WITH A PHARMACEUTICALLY ACCEPTABLE ACID

(71) Applicant: Les Laboratoires Servier, Suresnes (FR)

(72) Inventors: Jean-Luc Renaud, Bieville-Beauville (FR); Nicolas Pannetier, Caen (FR); Jean-Pierre Lecouve, Le Havre (FR); Lucile Vaysse-Ludot, St-Wandrille-Rancon (FR); Solenne Moulin, Saint-Brieuc (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 13/673,145

(22) Filed: Nov. 9, 2012

(65) Prior Publication Data

US 2013/0158256 A1 Jun. 20, 2013

(30) Foreign Application Priority Data

Dec. 20, 2011 (FR) ...................................... 11 03933

(51) Int. Cl.
*C07D 223/16* (2006.01)

(52) U.S. Cl.
USPC ........................................................ 540/523

(58) Field of Classification Search
USPC ........................................................ 540/523
See application file for complete search history.

(56) References Cited

U.S. PATENT DOCUMENTS

| 7,857,994 B2 | 12/2010 | Setlur et al. |
| 8,076,325 B2 | 12/2011 | Peglion et al. |
| 8,097,720 B2 | 1/2012 | Peglion et al. |

FOREIGN PATENT DOCUMENTS

| EP | 2036892 | 5/2009 |
| EP | 2202225 | 6/2010 |
| WO | WO2005/110993 | 11/2005 |

OTHER PUBLICATIONS

Bhor, et al., Tetrahedron Letters, vol. 49, No. 6, p. 968-969, Dec. 8. 2007.
French Preliminary Search Report for FR1103933 of Mar. 19, 2012.
S. Enthaler, Chemcatchem, vol. 2, p. 1411-1415, 2010.
T.C. Johnson, et al., Organometallics, vol. 30, p. 1859-1868, Mar. 2011.

*Primary Examiner* — Bruck Kifle
(74) *Attorney, Agent, or Firm* — Hueschen and Sage

(57) ABSTRACT

Process for the synthesis of ivabradine of formula (I):

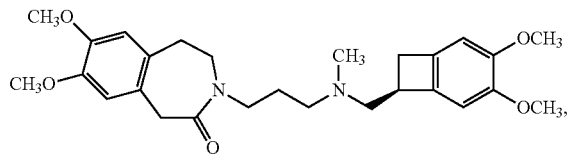

(I)

addition salts thereof with a pharmaceutically acceptable acid, and hydrates thereof.

15 Claims, No Drawings

PROCESS FOR THE SYNTHESIS OF IVABRADINE AND ADDITION SALTS THEREOF WITH A PHARMACEUTICALLY ACCEPTABLE ACID

The present invention relates to a process for the synthesis of ivabradine of formula (I):

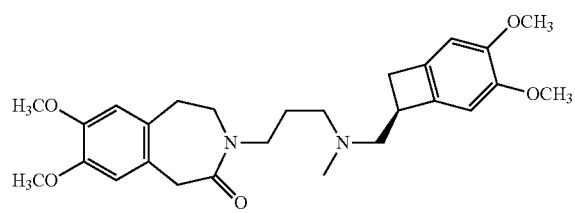

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one, addition salts thereof with a pharmaceutically acceptable acid, and hydrates thereof.

Ivabradine, and its addition salts with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also in various pathologies involving rhythm disturbances, especially supraventricular rhythm disturbances, and in heart failure.

The preparation and therapeutic use of ivabradine and its addition salts with a pharmaceutically acceptable acid, and more especially its hydrochloride, have been described in the European patent specification EP 0 534 859. Unfortunately, the ivabradine synthesis route described in that patent specification results in the expected product in a yield of only 1%.

Another ivabradine synthesis route, which is based on a reductive amination reaction, has been described in the European patent specification EP 1 589 005.

Reductive amination is a route that is a favoured approach for preparing amines. As this approach does not require isolation of the intermediate imine formed, this coupling reaction between an aldehyde and an amine in the presence of a reducing agent is widely used for the synthesis of compounds that are of value in the pharmaceutical or agrochemical fields and also in materials science.

The procedural protocols conventionally employed for carrying out reductive amination are:
 either use of stoichiometric amounts of hydride donors such as borohydrides ($NaBH_4$, $NaBH_3CN$ or $NaBH(OAc)_3$),
 or catalytic hydrogenation.

The use of hydride donors generates numerous waste products and the reagents in themselves are toxic.

In the case of catalytic hydrogenation, the fact that the reducing agent is molecular hydrogen is certainly of environmental value. The synthesis described in patent specification EP 1 589 005 follows this second route.

The patent specification EP 1 589 005 namely describes the synthesis of ivabradine hydrochloride starting from the compound of formula (II):

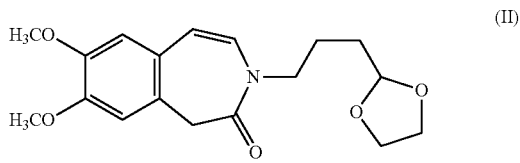 [SMILES: COc1cc2c(cc1OC)CC(=O)N(CCCC1OCCO1)C=C2]

which is subjected to a catalytic hydrogenation reaction in the presence of hydrogen and a palladium catalyst to yield the compound of formula (III):

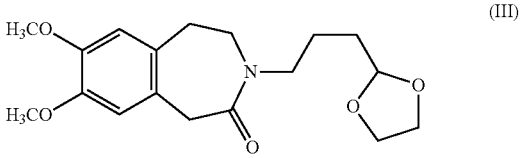 [SMILES: COc1cc2c(cc1OC)CC(=O)N(CCCC1OCCO1)CC2]

which, without being isolated, is reacted, in the presence of hydrogen and a palladium catalyst, with the compound of formula (IV):

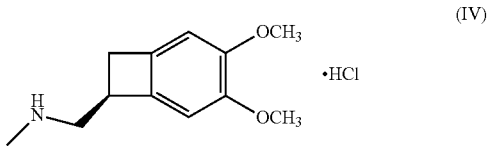

to yield ivabradine of formula (I), in hydrochloride form.

The disadvantage of that synthesis route is the use of a palladium catalyst.

Palladium, like rhodium, ruthenium or iridium, metals that are likewise used for catalysing reductive amination reactions, is a precious metal, the scarcity—and consequently high price—and also the toxicity of which limit its acceptability.

The present application describes an ivabradine synthesis route which makes it possible to dispense with the use of a precious metal.

The present invention relates namely to a process for the synthesis of ivabradine of formula (I):

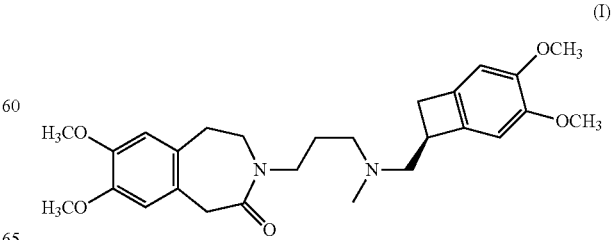

characterised in that the compound of formula (V):

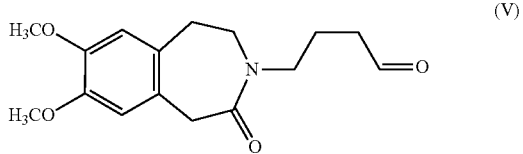 [SMILES: COc1cc2c(cc1OC)CC(=O)N(CCCC=O)CC2]

is subjected to a reductive amination reaction with the amine of formula (VI):

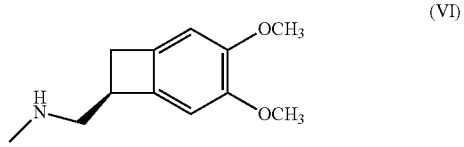

in the presence of an iron-based catalyst,
in the presence or not of trimethylamine N-oxide,
under dihydrogen pressure,
in an organic solvent or mixture of organic solvents.

Unlike precious metal compounds, iron compounds are usually non-toxic and iron salts are abundantly present in nature. They are metallic entities which are not harmful to the environment. The present invention proposes using metal complexes which are, in addition, easy to handle.

Iron complexes are known to catalyse reductive amination reactions in the presence of silylated hydrides (Enthaler S. *Chem Cat Chem* 2010, 2, 1411-1415) but there are only two examples in the literature which describe reductive amination based on catalytic hydrogenation (Bhanage B. M. et al *Tet. Lett.* 2008, 49, 965-969; Beller M. et al. *Chem Asian J.* 2011, 6, 2240-2245).

The operating conditions described by Bhanage require the presence of a water-soluble complex composed of an iron(II) salt and EDTA in a medium heated to a high temperature and under a high hydrogen pressure.

Applying the operating conditions described in that publication to the preparation of ivabradine did not enable the expected product to be obtained.

The following Table summarises the tests carried out in a 20-mL autoclave in the presence of 4 mL of degassed water, under 30 bars of hydrogen for 18 hours. The reactions were carried out at the scale of 0.5 mmol with an aldehyde/amine ratio of 1/1.5 (except for line 1: aldehyde/amine (1/1) and addition of 1% p-toluenesulphonic acid). The amounts in mol % are calculated with respect to the aldehyde.

NTf is the abbreviation for trifluoromethanesulphonamide.

TABLE 1

Results for reductive amination reactions catalysed by iron(II) salts

| | Iron(II) salt (mol %) | Amount (mol %) of EDTANa$_2$ | Temperature (°C.) | Findings |
|---|---|---|---|---|
| 1 | FeSO$_4$•7 H$_2$O (2) | 10 | 150 | 0% ivabradine-degradation |
| 2 | FeSO$_4$•7 H$_2$O (2) | 10 | 85 | 0% ivabradine |
| 3 | FeCl$_2$•4 H$_2$O (5) | 10 | 85 | 0% ivabradine |
| 4 | FeBr$_2$•4H$_2$O (5) | 10 | 85 | 0% ivabradine |
| 5 | Fe(BF$_4$)$_2$•6H$_2$O (5) | 10 | 85 | 0% ivabradine |
| 6 | Fe(NTf$_2$)$_2$•6H$_2$O (5) | 10 | 85 | 0% ivabradine |

The publication by Beller describes the reductive amination of various aldehydes by aniline derivatives in the presence of Fe$_3$(CO)$_{12}$ in toluene under 50 bars of hydrogen at 65° C.

Applying the operating conditions described in that publication to the preparation of ivabradine did not enable the expected product to be obtained.

The following Table summarises the tests, which were carried out in the presence of 1.7 mol % Fe$_3$(CO)$_{12}$ in various solvents at 65° C. under 25 bars of hydrogen for 18 hours.

The reactions were carried out in a 20-mL autoclave in the presence of 4 mL of degassed solvent.

The tests were conducted at the scale of 1 mmol with an aldehyde/amine ratio of 1/1 with 1% p-toluenesulphonic acid.

TABLE 2

Results for reductive amination reactions catalysed by Fe$_3$(CO)$_{12}$

| | Solvent | Findings |
|---|---|---|
| 1 | toluene | 0% ivabradine |
| 2 | dichloromethane | 0% ivabradine |
| 3 | tetrahydrofuran | 0% ivabradine |
| 4 | N-methylpyrrolidone | 0% ivabradine |

The iron-based catalyst used in the reaction for the reductive amination of the compound of formula (V) with the compound of formula (VI) preferably has the following general formula:

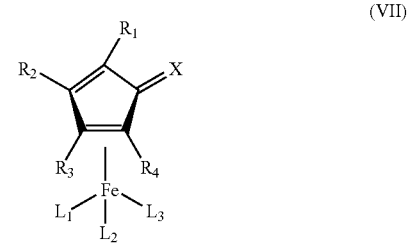

wherein R$_1$, R$_2$, R$_3$ and R$_4$ independently represent:
  a hydrogen atom, or
  a group —SiR$_5$R$_6$R$_7$, wherein R$_5$, R$_6$ and R$_7$ independently represent an optionally substituted, linear or branched (C$_1$-C$_6$)alkyl group or an optionally substituted aromatic or heteroaromatic group, or
  an optionally substituted aromatic or heteroaromatic group, or
  an optionally substituted, linear or branched (C$_1$-C$_6$)alkyl group, or
  an electron-attracting group, or
  an amine group that is aliphatic, aromatic, heteroaromatic or carrying an electron-attracting group, or
  an aliphatic, aromatic or heteroaromatic ether group,
  or the pairs R$_1$ and R$_2$, or R$_2$ and R$_3$, or R$_3$ and R$_4$ form, together with the carbon atoms carrying them, a 3- to 7-membered carbocycle or heterocycle,
X represents:
  an oxygen atom, or
  a —NH group or a nitrogen atom substituted by an aliphatic, aromatic, heteroaromatic or electron-attracting group, or
  a —PH group or a phosphorus atom substituted by one or more aliphatic, aromatic or electron-attracting groups, preferably forming a phosphine, phosphite, phosphonite, phosphoramidite, phosphinite, phospholane or phospholene group, or a sulphur atom, $L_1$, $L_2$ and $L_3$ independently represent a carbonyl, nitrile, isonitrile, heteroaromatic, phosphine, phosphite, phosphonite, phosphoramidite, phosphinite, phospholane, phospholene, aliphatic amine, aromatic amine, heteroaromatic amine, electron-attracting-group-carrying amine, aliphatic ether, aromatic ether, heteroaromatic ether, sulphone, sulphoxide or sulphoximine group or an N-heterocyclic carbene group having one of the two following formulae:

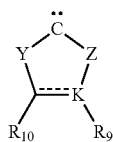

wherein Y and Z independently represent a sulphur or oxygen atom or a group $NR_8$ wherein $R_8$ represents an optionally substituted alkyl group or an optionally substituted aromatic or heteroaromatic group, K represents a carbon or nitrogen atom, $R_9$ and $R_{10}$ independently represent a hydrogen atom, an optionally substituted alkyl group, an optionally substituted aromatic or heteroaromatic group, a halogen atom, an aliphatic, aromatic or heteroaromatic ether group, an aliphatic, aromatic or heteroaromatic amine group, or the pair $R_9$ and $R_{10}$ form, together with the atoms carrying them, a 3- to 7-membered carbocycle or heterocycle, or

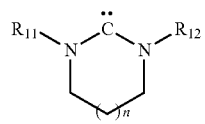

wherein $R_{11}$ and $R_{12}$ independently represent an optionally substituted alkyl group or an optionally substituted aromatic or heteroaromatic group and n is 1 or 2.

An electron-attracting group is a group which attracts electrons more than a hydrogen atom occupying the same position in the molecule would.

Among the electron-attracting groups there may be mentioned, without implying any limitation, the following groups: ester, acid, nitrile, aldehyde, ketone, amide, nitro, sulphone, sulphoxide, sulphoximine, sulphonamide or phosphoric diester.

In an embodiment of the invention, the iron-based catalyst used in the reaction for the reductive amination of the compound of formula (V) with the compound of formula (VI) has the following general formula:

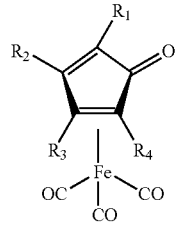

(VIII)

wherein $R_2$ and $R_3$ each represent a hydrogen atom or form, together with the carbon atoms carrying them, a 3- to 7-membered carbocycle or heterocycle, and $R_1$ and $R_4$ independently represent:

either a group $-SiR_5R_6R_7$, wherein $R_5$, $R_6$ and $R_7$ independently represent an optionally substituted, linear or branched $(C_1-C_6)$alkyl group or an optionally substituted aryl group, or an optionally substituted aromatic or heteroaromatic group, or an optionally substituted, linear or branched $(C_1-C_6)$ alkyl group.

The catalyst of formula (VIII) used in the reaction for the reductive amination of the compound of formula (V) with the compound of formula (VI) is preferably selected from the following catalysts:

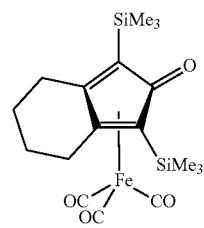

(IX)

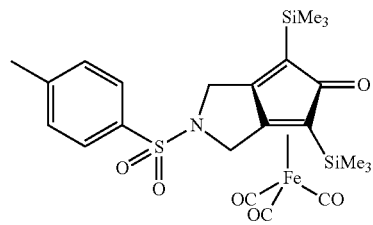

(X)

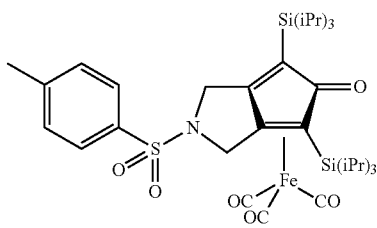

(XI)

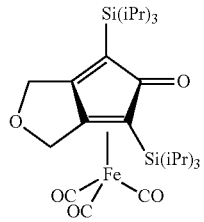

(XII)

In another embodiment of the invention, the iron-based catalyst used in the reaction for the reductive amination of the compound of formula (V) with the compound of formula (VI) has the following general formula:

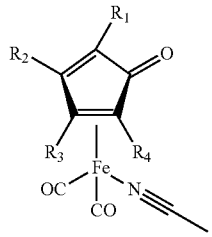

(XIII)

wherein $R_2$ and $R_3$ each represent a hydrogen atom or form, together with the carbon atoms carrying them, a 3- to 7-membered carbocycle or heterocycle, and $R_1$ and $R_4$ independently represent:

- either a group —$SiR_5R_6R_7$, wherein $R_5$, $R_6$ and $R_7$ independently represent an optionally substituted, linear or branched ($C_1$-$C_6$)alkyl group or an optionally substituted aromatic or heteroaromatic group,
- or an optionally substituted aromatic or heteroaromatic group,
- or an optionally substituted, linear or branched ($C_1$-$C_6$) alkyl group.

The catalyst of formula (XIII) used in the reaction for the reductive amination of the compound of formula (V) with the compound of formula (VI) is preferably selected from the following catalysts:

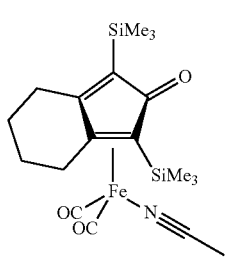

(XIV)

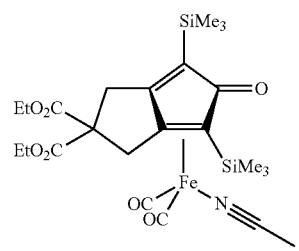

(XV)

In another embodiment of the invention, the iron-based catalyst used in the reaction for the reductive amination of the compound of formula (V) with the compound of formula (VI) has the following formula:

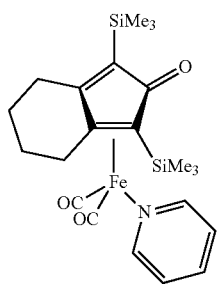

(XVI)

In another embodiment of the invention, the iron-based catalyst used in the reaction for the reductive amination of the compound of formula (V) with the compound of formula (VI) has the following formula:

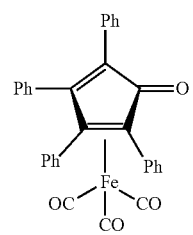

(XVII)

The amount of catalyst used in the reaction for the reductive amination of the compound of formula (V) with the compound of formula (VI) is from 1 mol % to 10 mol % relative to the aldehyde.

The amount of trimethylamine N-oxide used in the reaction for the reductive amination of the compound of formula (V) with the compound of formula (VI) is from 0 to 3 equivalents relative to the catalyst, more preferably from 0.5 to 1.5 equivalents relative to the catalyst.

The dihydrogen pressure in the reaction for the reductive amination of the compound of formula (V) with the compound of formula (VI) is preferably from 1 to 20 bars, more preferably from 1 to 10 bars, and even more preferably from 1 to 5 bars.

Among the solvents that may be used for carrying out the reaction for the reductive amination of the compound of formula (V) with the compound of formula (VI) there may be mentioned, without implying any limitation, alcohols, preferably ethanol, isopropanol, trifluoroethanol, tert-butanol or methanol, tetrahydrofuran, ethyl acetate, acetonitrile and dioxane.

The solvent preferably used for carrying out the reaction for the reductive amination of the compound of formula (V) with the compound of formula (VI) is ethanol.

The temperature of the reductive amination reaction between the compound of formula (V) and the compound of formula (VI) is preferably from 25 to 100° C., more preferably from 50 to 100° C., and even more preferably from 80 to 100° C.

The Examples hereinbelow illustrate the invention.

The column chromatography purification procedures are carried out on 70-230 mesh silica gel.

The $^1$H NMR spectra are recorded at 400 MHz.

The chemical shifts are expressed in ppm (internal reference: TMS).

The following abbreviations have been used to describe the peaks: singlet (s), doublet (d), doublet of doublets (dd), triplet (t), quadruplet (q), multiplet (m).

The catalysts used in the process of the invention can be prepared in accordance with the methods described in the following publications: *Synlett* 1992, pp 1002-1004, *Synlett* 1993, pp 924-926 and *Advanced Synthesis and Catalysis* 2012, 354 (4), pp 597-601.

General Procedure A for Preparation of 3-{3-[{[(7S)-3,4-dimethoxybicyclo[4.2.0]octa-1,3,5-trien-7-yl]methyl}(methyl)amino]propyl}-7,8-dimethoxy-1,3,4,5-tetrahydro-2H-3-benzazepin-2-one 1 mmol of [(7S)-3,4-dimethoxybicyclo[4.2.0]octa-1,3,5-trien-7-yl]-N-methylmethanamine and 1 mmol of 3-(7,8-dimethoxy-2-oxo-1,2,4,5-tetrahydro-3H-3-benzazepin-3-yl)propanal are introduced into a clean and dry stainless-steel autoclave under an argon atmosphere. The mixture is degassed by three vacuum/argon cycles, and 2 mL of distilled and degassed ethanol are added. The solution is stirred at 85° C. for one hour.

A mixture of 5 mol % of iron complex and 5 mol % of trimethylamine N-oxide in 1 mL of ethanol is prepared over 30 minutes in a Schlenk tube under an argon atmosphere and then introduced into the autoclave.

The autoclave is then placed under hydrogen pressure (5 bars) and the reaction mixture is stirred at 85° C. for 16 hours and the autoclave is then returned to ambient temperature and decompressed.

The reaction mixture is filtered over deactivated neutral alumina (3% water) using ethyl acetate as solvent.

The crude product is purified on silica gel (eluant: pentane/ethyl acetate (95/5) with 0.5% triethylamine) to obtain the expected product.

General Procedure B for Preparation of 3-{3-[{[(7S)-3,4-dimethoxybicyclo[4.2.0]octa-1,3,5-trien-7-yl]methyl}(methyl)amino]propyl}-7,8-dimethoxy-1,3,4,5-tetrahydro-2H-3-benzazepin-2-one 1 mmol of [(7S)-3,4-dimethoxybicyclo[4.2.0]octa-1,3,5-trien-7-yl]-N-methylmethanamine and 1 mmol of 3-(7,8-dimethoxy-2-oxo-1,2,4,5-tetrahydro-3H-3-benzazepin-3-yl)propanal are introduced into a clean and dry stainless-steel autoclave under an argon atmosphere. The mixture is degassed by three vacuum/argon cycles and 3 mL of distilled and degassed ethanol are added. The solution is stirred at 85° C. for one hour. The iron complex (5 mol %) is added under argon. The autoclave is then placed under hydrogen pressure (5 bars) and the reaction mixture is stirred at 85° C. for 16 hours and then the autoclave is returned to ambient temperature and decompressed.

The reaction mixture is filtered over deactivated neutral alumina (3% water) using ethyl acetate as solvent.

The crude product is purified on silica gel (eluant: pentane/ethyl acetate (95/5) with 0.5% triethylamine) to obtain the expected product.

EXAMPLE 1

3-{3-[{[(7S)-3,4-Dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one is prepared according to general procedure A in the presence of the iron catalyst of formula (IX).

Yield=61%

$^1$H NMR (CDCl$_3$): δ=6.67 and 6.64 (2s, 2H); 6.55 and 6.50 (2s, 2H); 3.79 and 3.78 (2s, 12H); 3.76 (s, 2H); 3.67 (m, 2H); 3.45 (m, 3H); 3.17 (dd, 1H); 2.99 (m, 2H); 2.65 (m, 2H); 2.50 (dd, 1H); 2.37 (t, 2H); 2.26 (s, 3H); 1.72 (q, 2H).

EXAMPLE 2

3-{3-[{[(7S)-3,4-Dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one is prepared according to general procedure A in the presence of the iron catalyst of formula (X).

Yield=63%

EXAMPLE 3

3-{3-[{[(7S)-3,4-Dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one is prepared according to general procedure A in the presence of the iron catalyst of formula (XI).

Yield=79%

EXAMPLE 4

3-{3-[{[(7S)-3,4-Dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one is prepared according to general procedure A in the presence of the iron catalyst of formula (XII).

Yield=68%

EXAMPLE 5

3-{3-[{[(7S)-3,4-Dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one is prepared according to general procedure B in the presence of the iron catalyst of formula (XIV).

Yield=68%

EXAMPLE 6

3-{3-[{[(7S)-3,4-Dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one is prepared according to general procedure B in the presence of the iron catalyst of formula (XV).

Yield=68%

EXAMPLE 7

3-{3-[{[(7S)-3,4-Dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one is prepared according to general procedure B in the presence of the iron catalyst of formula (XVI).

Yield=59%

EXAMPLE 8

3-{3-[{[(7S)-3,4-Dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one is prepared according to general procedure B in the presence of the iron catalyst of formula (XVII).

Yield=48%

The invention claimed is:

1. A process for the synthesis of ivabradine of formula (I):

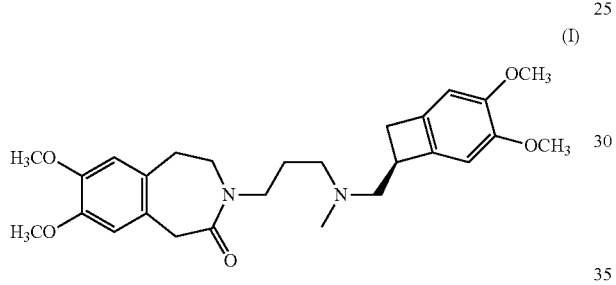

(I)

wherein a compound of formula (V):

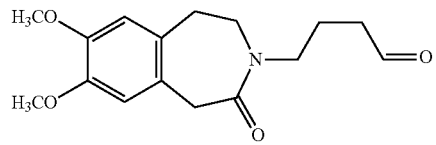

(V)

is subjected to a reductive amination reaction with an amine of formula (VI):

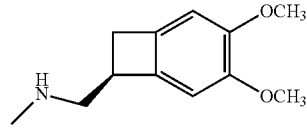

(VI)

in the presence of an iron-based catalyst,
optionally in the presence of trimethylamine N-oxide,
under dihydrogen pressure of from 1 to 20 bars,
in an organic solvent or mixture of organic solvents,
at a temperature from 25 to 100° C.

2. The process according to claim 1, wherein the iron-based catalyst has the following general formula:

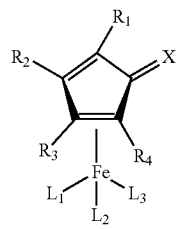

(VII)

wherein $R_1$, $R_2$, $R_3$ and $R_4$ independently represent:
- a hydrogen atom,
- an —$SiR_5R_6R_7$ group, wherein $R_5$, $R_6$ and $R_7$ independently represent an optionally substituted, linear or branched ($C_1$-$C_6$)alkyl group or an optionally substituted aromatic or heteroaromatic group,
- an optionally substituted aromatic or heteroaromatic group,
- an optionally substituted, linear or branched ($C_1$-$C_6$) alkyl group,
- an electron-attracting group,
- an amine group that is aliphatic, aromatic, heteroaromatic or carrying an electron-attracting group, or
- an aliphatic, aromatic or heteroaromatic ether group, or the pairs $R_1$ and $R_2$, or $R_2$ and $R_3$, or $R_3$ and $R_4$, together with the carbon atoms to which they are attached, form a 3- to 7-membered carbocycle or heterocycle, X represents:
- an oxygen atom,
- an —NH group or a nitrogen atom substituted by an aliphatic, aromatic, heteroaromatic or electron-attracting group,
- a —PH group or a phosphorus atom substituted by one or more aliphatic, aromatic or electron-attracting groups, or
- a sulphur atom, $L_1$, $L_2$ and $L_3$ independently represent a carbonyl, nitrile, isonitrile, heteroaromatic, phosphine, phosphite, phosphonite, phosphoramidite, phosphinite, phospholane, phospholene, aliphatic amine, aromatic amine, heteroaromatic amine, electron-attracting-group-carrying amine, aliphatic ether, aromatic ether, heteroaromatic ether, sulphone, sulphoxide or sulphoximine group or an N-heterocyclic carbene group having one of the two following formulae:

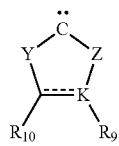

wherein Y and Z independently represent a sulphur or oxygen atom or an $NR_8$ group wherein $R_8$ represents an optionally substituted alkyl group or an optionally substituted aromatic or heteroaromatic group, K represents a carbon or nitrogen atom, $R_9$ and $R_{10}$ independently represent a hydrogen atom, an optionally substituted alkyl group, an optionally substituted aromatic or heteroaromatic group, a halogen atom, an aliphatic, aromatic or heteroaromatic ether group, an aliphatic, aromatic or heteroaromatic amine group, or the pair $R_9$ and $R_{10}$, together with the atoms to which they are attached, form a 3- to 7-membered carbocycle or heterocycle, or

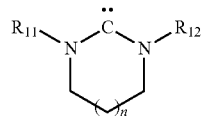

wherein $R_{11}$ and $R_{12}$ independently represent an optionally substituted alkyl group or an optionally substituted aromatic or heteroaromatic group and n is 1 or 2.

3. The process according to claim 2, wherein the iron-based catalyst has the following general formula:

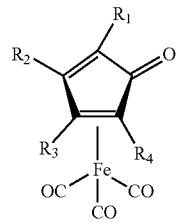

(VIII)

wherein $R_2$ and $R_3$ each represent a hydrogen atom or, together with the carbon atoms to which they are attached, form a 3- to 7-membered carbocycle or heterocycle, and $R_1$ and $R_4$ independently represent:

an —$SiR_5R_6R_7$ group, wherein $R_5$, $R_6$ and $R_7$ independently represent an optionally substituted, linear or branched ($C_1$-$C_6$)alkyl group or an optionally substituted aryl group, an optionally substituted aromatic or heteroaromatic group, or an optionally substituted, linear or branched ($C_1$-$C_6$) alkyl group.

4. The process according to claim 3, wherein the iron-based catalyst is selected from:

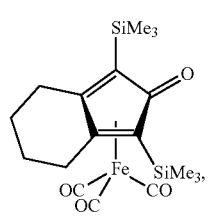

(IX)

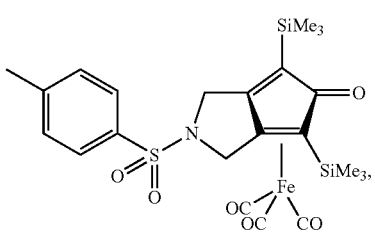

(X)

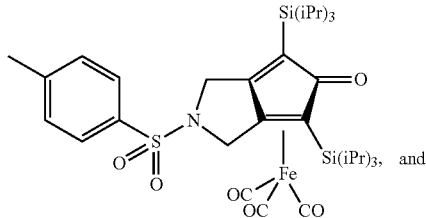

(XI)

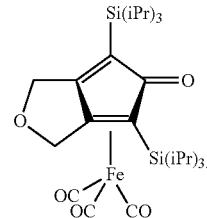

(XII)

5. The process according to claim 2, wherein the iron-based catalyst has the following general formula:

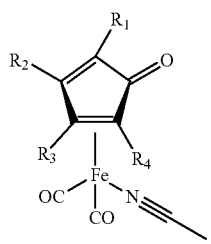

(XIII)

wherein $R_2$ and $R_3$ each represent a hydrogen atom or, together with the carbon atoms to which they are attached, form a 3- to 7-membered carbocycle or heterocycle, and $R_1$ and $R_4$ independently represent:

an —$SiR_5R_6R_7$ group, wherein $R_5$, $R_6$ and $R_7$ independently represent an optionally substituted, linear or branched ($C_1$-$C_6$)alkyl group or an optionally substituted aromatic or heteroaromatic group, an optionally substituted aromatic or heteroaromatic group, or an optionally substituted, linear or branched ($C_1$-$C_6$) alkyl group.

6. The process according to claim 5, wherein the iron-based catalyst is selected from:

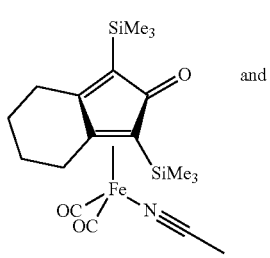

(XIV)

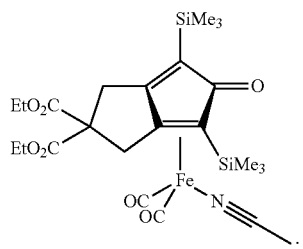

(XV)

7. The process according to claim 2, wherein the iron-based catalyst has the following formula:

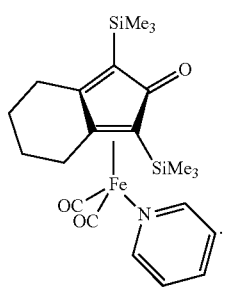

(XVI)

8. The process according to claim 2, wherein the iron-based catalyst has the following formula:

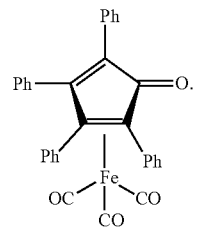

(XVII)

9. The process according to claim 1, wherein the amount of catalyst used in the reductive amination reaction is from 1 mol % to 10 mol % relative to the aldehyde.

10. The process according to claim 1, wherein the amount of trimethylamine N-oxide used in the reductive amination reaction is from 0 to 3 equivalents relative to the catalyst.

11. The process according to claim 10, wherein the amount of trimethylamine N-oxide used in the reductive amination reaction is from 0.5 to 1.5 equivalents relative to the catalyst.

12. The process according to claim 1, wherein the dihydrogen pressure in the reductive amination reaction is from 1 to 10 bars.

13. The process according to claim 1, wherein the solvent in the reductive amination reaction is an alcohol.

14. The process according to claim 13, wherein the solvent in the reductive amination reaction is ethanol.

15. The process according to claim 1, wherein the temperature of the reductive amination reaction is from 50 to 100° C.

* * * * *

UNITED STATES PATENT AND TRADEMARK OFFICE
CERTIFICATE OF CORRECTION

PATENT NO. : 8,513,410 B2
APPLICATION NO. : 13/673145
DATED : August 20, 2013
INVENTOR(S) : Jean-Luc Renaud et al.

It is certified that error appears in the above-identified patent and that said Letters Patent is hereby corrected as shown below:

Title Page, References Cited, Column 2: "7,857,994 B2   12/2010" should be
--7,857,994 B2 01/2011--.

Title Page, References Cited, Column 2: "EP 2036892 5/2009" should be
--EP 2036892 3/2009--.

Title Page, References Cited, under Other Publications, Bhor et al.: "p. 968-969" should be
--p. 965-969--.

Signed and Sealed this
Fifteenth Day of October, 2013

Teresa Stanek Rea
*Deputy Director of the United States Patent and Trademark Office*